US008414632B2

(12) United States Patent
Kornkven Volk et al.

(10) Patent No.: US 8,414,632 B2

(45) Date of Patent: Apr. 9, 2013

(54) ADJUSTABLE CATHETER TIP

(75) Inventors: Angela Kornkven Volk, Rogers, MN (US); Karl A. Jagger, Deephaven, MN (US); Tracee Eidenschink, Wayzata, MN (US); Richard Olson, Blaine, MN (US); John Blix, Maple Grove, MN (US); Derek Sutermeister, Eden Prairie, MN (US); Jay Rassat, Buffalo, MN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 2105 days.

(21) Appl. No.: 11/368,927

(22) Filed: Mar. 6, 2006

(65) Prior Publication Data

US 2007/0208276 A1 Sep. 6, 2007

(51) Int. Cl.
*A61F 2/06* (2006.01)
*A61M 29/00* (2006.01)

(52) U.S. Cl.
USPC ........................... 623/1.11; 606/192; 606/194

(58) Field of Classification Search ................. 623/1.11, 623/1.12, 1.23; 606/108, 192, 194
See application file for complete search history.

(56) References Cited

U.S. PATENT DOCUMENTS

| | | | | |
|---|---|---|---|---|
| 4,921,483 | A | 5/1990 | Wijay et al. | 604/96 |
| 5,026,377 | A | 6/1991 | Burton et al. | 606/108 |
| 5,534,007 | A | 7/1996 | St. Germain et al. | 606/108 |
| 5,573,520 | A | 11/1996 | Schwartz et al. | 684/282 |
| 5,855,565 | A | 1/1999 | Bar-Cohen et al. | 604/104 |
| 6,113,579 | A * | 9/2000 | Eidenschink et al. | 604/264 |
| 6,117,296 | A | 9/2000 | Thomson | 204/607 |
| 6,120,522 | A | 9/2000 | Vrba et al. | 606/190 |
| 6,123,718 | A | 9/2000 | Tu et al. | 607/113 |
| 6,249,076 | B1 * | 6/2001 | Madden et al. | 310/363 |
| 6,388,043 | B1 | 5/2002 | Langer et al. | 528/80 |
| 6,514,237 | B1 * | 2/2003 | Maseda | 604/533 |
| 6,620,527 | B2 | 9/2003 | Wang | 428/654 |
| 6,626,934 | B2 | 9/2003 | Blaeser et al. | 623/1.11 |
| 6,679,836 | B2 | 1/2004 | Couvillon, Jr. | 600/146 |
| 6,749,556 | B2 | 6/2004 | Banik | 600/30 |
| 6,770,027 | B2 | 8/2004 | Banik et al. | 600/146 |
| 6,790,221 | B2 | 9/2004 | Monroe et al. | 623/1.11 |
| 6,812,624 | B1 | 11/2004 | Pei et al. | 310/800 |
| 6,835,173 | B2 | 12/2004 | Couvillon, Jr. | 600/146 |
| 6,921,360 | B2 | 7/2005 | Banik | 600/30 |
| 6,940,211 | B2 | 9/2005 | Pelrine et al. | 310/330 |

(Continued)

FOREIGN PATENT DOCUMENTS

| | | |
|---|---|---|
| EP | 0371486 | 6/1990 |
| WO | WO 2004/014238 | 2/2004 |

OTHER PUBLICATIONS

U.S. Appl. No. 11/280,120, filed Nov. 16, 2005, Weber et al.
U.S. Appl. No. 11/411,360, filed Apr. 25, 2006, Komkven Volk et al.

(Continued)

*Primary Examiner* — Gary Jackson
*Assistant Examiner* — Jonathan Hollm
(74) *Attorney, Agent, or Firm* — Vidas, Arrett & Steinkraus, P.A.

(57) ABSTRACT

A catheter tip has an outer surface section, an inner surface section, a spatial configuration and at least one segment of electroactive polymer. The inner surface section defines a guide wire lumen. The electroactive polymer has an actuated state and a non-actuated state. In an actuated state, the electroactive polymer alters the spatial configuration of the catheter tip.

15 Claims, 15 Drawing Sheets

10
20a 20b 20c
16
20a 20b 20c

U.S. PATENT DOCUMENTS

| | | | | |
|---|---|---|---|---|
| 6,982,514 | B1 | 1/2006 | Lu et al. | 310/300 |
| 6,997,870 | B2 | 2/2006 | Couvillon, Jr. | 600/146 |
| 7,063,671 | B2 | 6/2006 | Couvillon, Jr. | 600/562 |
| 2002/0052641 | A1 * | 5/2002 | Monroe et al. | 623/1.11 |
| 2003/0099684 | A1 | 5/2003 | Domb | 424/426 |
| 2003/0236445 | A1 | 12/2003 | Couvillon, Jr. | 600/114 |
| 2003/0236531 | A1 | 12/2003 | Couvillon | |
| 2004/0068161 | A1 | 4/2004 | Couvillon, Jr. | 600/143 |
| 2004/0087982 | A1 | 5/2004 | Eskuri | 606/153 |
| 2004/0138733 | A1 * | 7/2004 | Weber et al. | 623/1.11 |
| 2004/0143160 | A1 | 7/2004 | Couvillon, Jr. | 600/114 |
| 2005/0004425 | A1 | 1/2005 | Banik | 600/30 |
| 2005/0085693 | A1 | 4/2005 | Belson et al. | 600/146 |
| 2005/0102017 | A1 | 5/2005 | Mattison | 623/1.11 |
| 2005/0107669 | A1 | 5/2005 | Couvillon, Jr. | 600/146 |
| 2005/0119213 | A1 | 6/2005 | Khachigian | 514/44 |
| 2005/0165439 | A1 | 7/2005 | Weber et al. | 606/191 |
| 2005/0183259 | A1 | 8/2005 | Eidenschink et al. | 29/508 |
| 2005/0187536 | A1 | 8/2005 | Shelso et al. | 604/528 |
| 2006/0041264 | A1 | 2/2006 | Eskuri | 606/153 |
| 2006/0111618 | A1 | 5/2006 | Couvillon, Jr. | 600/152 |
| 2007/0142771 | A1 * | 6/2007 | Durcan | 604/103.06 |

OTHER PUBLICATIONS

D. Zhou et al., "Actuators for the Cochlear Implant," *Synthetic Metals* 135-136 (2003) 39-40.

E. Smela et al., "Thiol Modified Pyrrole Monomers: 1. Synthesis, Characterization, and Polymerization of 1-(2-Thioethyl)-Pyrrole and 3-(2-Thioethyl)-Pyrrole," *Langmuir*, 14 (11), 2970-2975, 1998.

E.W.H. Jager, E. Smela, O. Inganas, "Microfabricating Conjugated Polymer Actuators," *Science*, 290, 1540-1545, 2000.

E. Smela, M. Kaltenbach, and J. Holdenried, "Electrochemically Driven Polypyrrole Bilayers for Moving and Positioning Bulk Micromachined Silicon Plates," *J. Microelectromechanical Systems*, 8(4), 373-383, 1999.

*Proceedings of the SPIE*, vol. 4329 (2001) entitled "Smart Structures and Materials" 2001. see Madden et al., "Polypyrrole actuators: modeling and performance," pp. 73-83.

Yoshioka et al., "Epoxy-based Electroactive Polymer Gels," vol. 42, No. 4, pp. 404-408, Dec. 2002.

Electroactive Muscle/Materials Selection www.me.berkeley.edu/ME117/S05/ finalproject/pdf/Electroactive_Muscle.pdf.

* cited by examiner

ADJUSTABLE CATHETER TIP

CROSS-REFERENCE TO RELATED APPLICATIONS

Not Applicable

STATEMENT REGARDING FEDERALLY SPONSORED RESEARCH

Not Applicable

FIELD OF THE INVENTION

In some embodiments, this invention relates to delivery systems, such as catheter systems of all types, which are utilized in the delivery of implantable devices. Specifically, this invention relates to catheter tips.

BACKGROUND OF THE INVENTION

Catheters are thin flexible tubes which are introduced into a vein or artery and guided to selected sites in the vascular system. Angiographic catheters are employed to inject contrast media into a vessel to visualize the shape, state, topography, functionality and other characteristics of the vessel for the purpose of diagnosing anatomic abnormalities of an organ and its conduits. Such catheters are used, for instance, to diagnose diseases of the heart and the circulatory system.

The guidance of a catheter within a tortuous vessel structure, such as a coronary artery and the arteries supplying the brain, often present difficult challenges. Efficient guidance of the distal portion of the catheter may be achieved by various means, including the use of a guide wire (essentially a long, slim and flexible wire or coil on which the catheter's lumen rides or slides to the desired location) or a specially designed catheter tip.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All US patents and applications and all other published documents mentioned anywhere in this application are incorporated herein by reference in their entirety.

Without limiting the scope of the invention, a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

In at least one embodiment, the invention is directed to a catheter tip with a shaft comprising an outer surface section, an inner surface section and at least one section of electroactive polymer (EAP). The EAP has an actuated state and a non-actuated state. The section of EAP can be any desired width, length and depth depending upon the effect desired when the EAP is in an actuated state. In at least one embodiment, the at least one section of EAP is positioned within the inner surface section. In one embodiment, the at least one section of EAP, positioned within the inner surface section, volumetrically expands when in an actuated state. In another embodiment, the at least one section of EAP is positioned within the inner surface section and volumetrically contracts when in an actuated state.

In at least one embodiment, the at least one section of EAP is positioned within the outer surface section. In one embodiment, the at least one section of EAP, positioned within the outer surface section, volumetrically expands when in an actuated state. In at least one embodiment, the catheter tip has four longitudinal sections of EAP positioned within the outer surface section that volumetrically expand when actuated thereby engaging the catheter tip with the vessel wall when in use. In one embodiment, the four longitudinal section of EAP are engaged to the exterior of the catheter tip. In one embodiment, the EAP in an actuated state affects the stiffness of the catheter tip and allows for either CTO or varying vessel tortuousness. In another embodiment, the at least one section of EAP is positioned within the outer surface section and volumetrically contracts when in an actuated state.

In at least one embodiment, the at least one section of EAP forms at least a portion of the catheter tip shaft. In at least one embodiment, the at least one section of EAP is positioned at the distal end region of the catheter tip and volumetrically expands when actuated, causing the catheter tip to flare. In at least one embodiment, the at least one section of EAP is positioned at the proximal end region of the catheter tip and volumetrically expands when actuated.

In at least one embodiment, the catheter tip and catheter shaft are manufactured as one unit. In at least one embodiment, a catheter tip manufactured of electroactive polymer is engaged to inner shaft of a self-expanding stent delivery system. In at least one embodiment, a catheter tip manufactured of electroactive polymer can be attached to a sheath covering a self-expanding stent. In at least one embodiment, a catheter tip manufactured of electroactive polymer is integrated with the exterior sheath. In at least one embodiment, a catheter assembly with the inventive catheter tip is used to deploy an implantable device. In at least one embodiment, a catheter assembly with the inventive catheter tip is used to deploy a stent.

In at least one embodiment, a balloon catheter is provided in which the distal end of the balloon is engaged to an inventive tip and the proximal end of the balloon is engaged to the catheter. Typically, the catheter will not have any other tube extending within in the region of the balloon.

In another embodiment, a balloon catheter is provided in which the distal end of the balloon is engaged to an inventive tip and the proximal end of the balloon is engaged to the catheter. The balloon catheter is provided with a slidable inner shaft therein.

It is within the scope of the invention for the inventive tips disclosed herein to be made in part of an EAP or in their entirety of EAP.

These and other embodiments which characterize the invention are pointed out with particularity in the claims annexed hereto and forming a part hereof. However, for further understanding of the invention, the advantages and objectives obtained by its use, reference should be made to the drawings which form a further part hereof and the accompanying descriptive matter, in which there is illustrated and described an embodiments of the invention.

BRIEF DESCRIPTION OF THE SEVERAL VIEWS OF THE DRAWING(S)

A detailed description of the invention is hereafter described with specific reference being made to the drawings.

FIG. 1*a* depicts how EAP can increase or decrease from an initial length when actuated FIG. 1*b* depicts how EAP can bend when actuated.

FIG. 1*c* depicts how EAP can increase or decrease from an initial size when actuated.

Figure 4A:
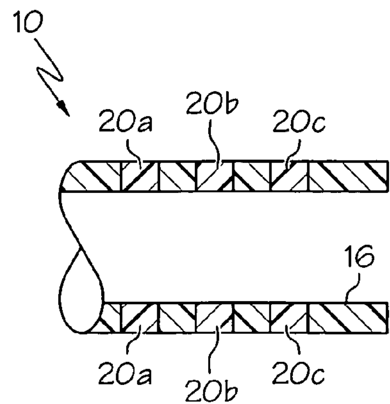

FIG. 4*a* shows a longitudinal cross section of a catheter tip with three circumferential bands of electroactive polymer forming a portion of the catheter tip shaft.

Figure 4B:
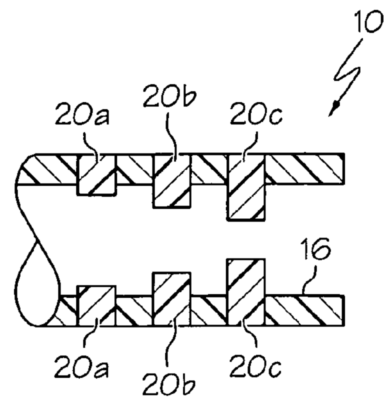

FIG. 4*b* shows the catheter tip of FIG. 4*a* with the circumferential bands of electroactive polymer in an actuated state.

Figure 3:
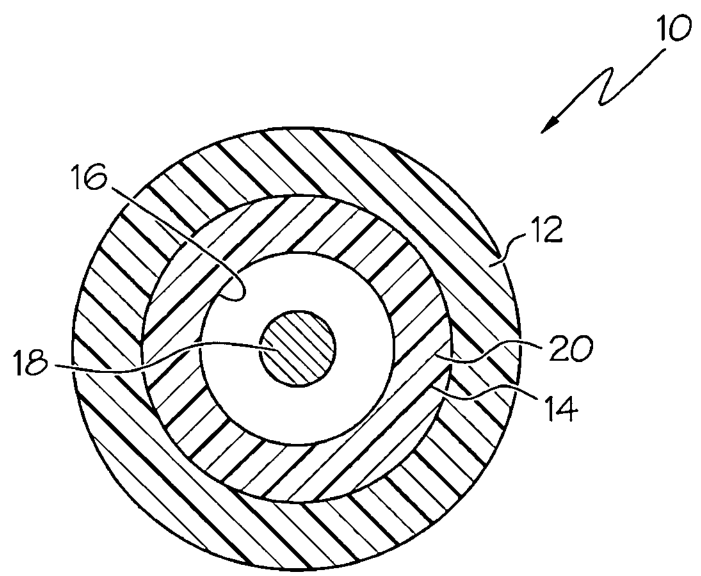
FIG. 3 is a cross section of the catheter in FIG. 2, with the inventive catheter tip, at line 2-2 with a circumferential band of electroactive polymer in the inner surface section of the catheter tip.
Figure 5:
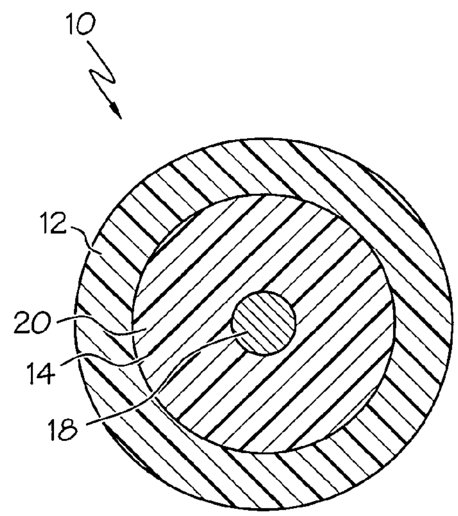

FIG. 5 shows the cross-section of FIG. 3 with the electroactive polymer in an actuated state engaging the guide wire.

Figure 6:
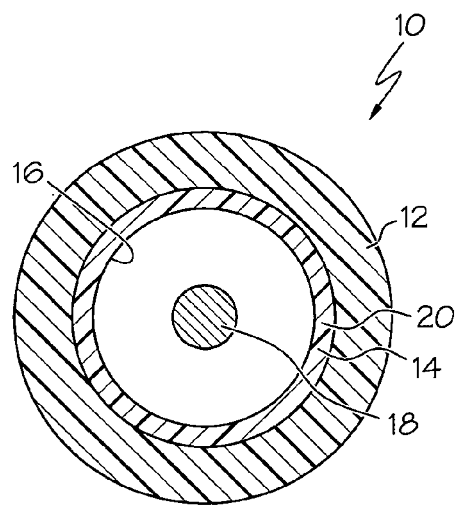

FIG. 6 shows the cross-section of FIG. 3 with the electroactive polymer in an actuated state, causing the guide wire lumen to increase in size.

Figure 7A:
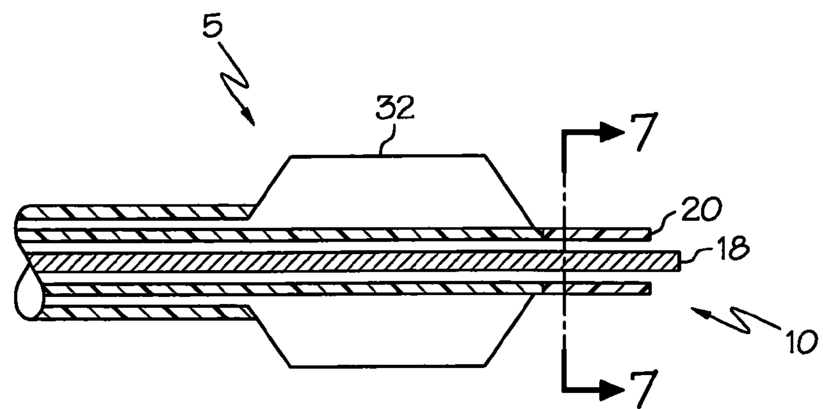

FIG. 7*a* is a longitudinal cross section of a balloon catheter where the tip or distal end region of the balloon catheter has a section of electroactive polymer.

Figure 7B:
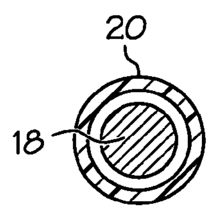

FIG. 7*b* is a cross section of the tip of the catheter in FIG. 6*a*, taken at line 6-6, with a large diameter guide wire.

Figure 7C:
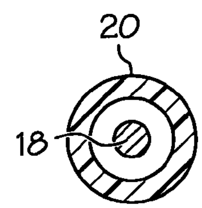

FIG. 7*c* is a cross section of the tip of the catheter in FIG. 6*a*, taken at line 6-6, with the electroactive polymer in an actuated state which allows a small diameter guide wire to be used with the catheter tip.

Figure 8:
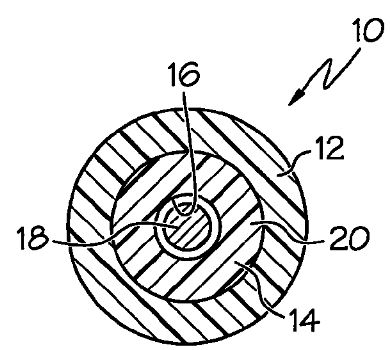

FIG. 8 shows the cross section of FIG. 3 with the electroactive polymer in an actuated state, which causes the guide wire lumen to decrease in size.

Figure 9:
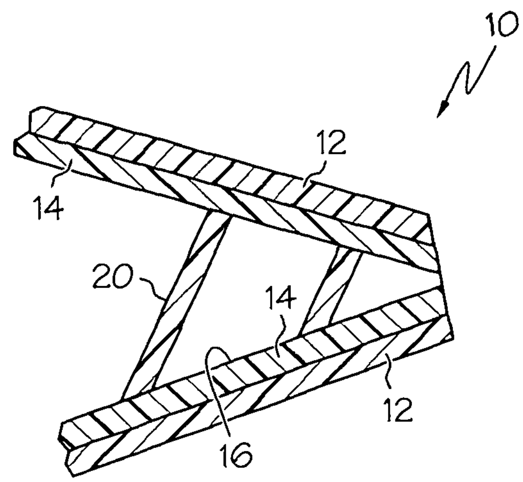

FIG. 9 is a longitudinal cross section of the inventive catheter tip with a coil of electroactive polymer forming a portion of the inner section of the catheter tip.

Figure 10A:
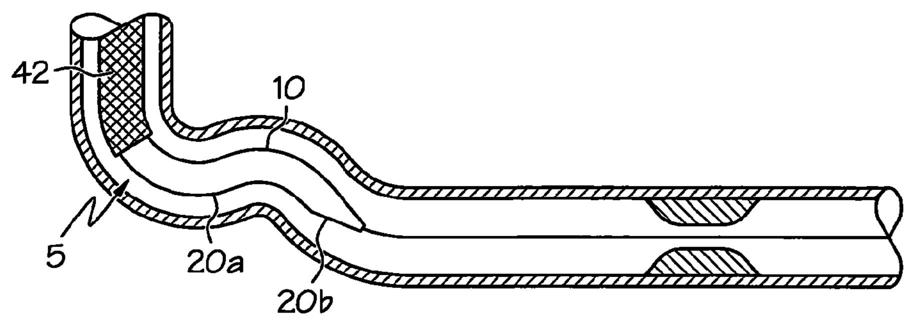

FIG. 10*a* shows the catheter tip in non-actuated state crossing a tortuous region.

Figure 10B:
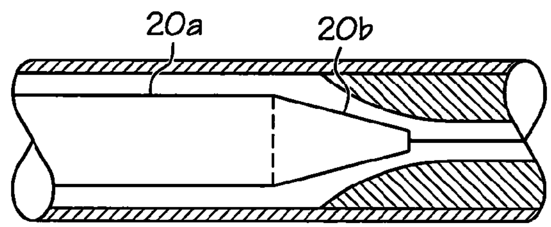

FIG. 10*b* shows the actuated state of the catheter tip in FIG. 10*a* as it approaches a chronic total occlusion where region A gains more mass and stiffness than region B and can be selected on or off independently.

Figure 2:
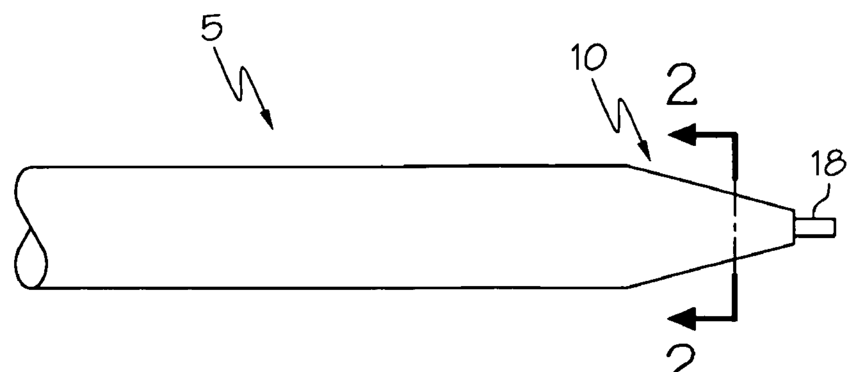
FIG. 2 is a side view of the distal end of a catheter with a catheter tip.
Figure 11:
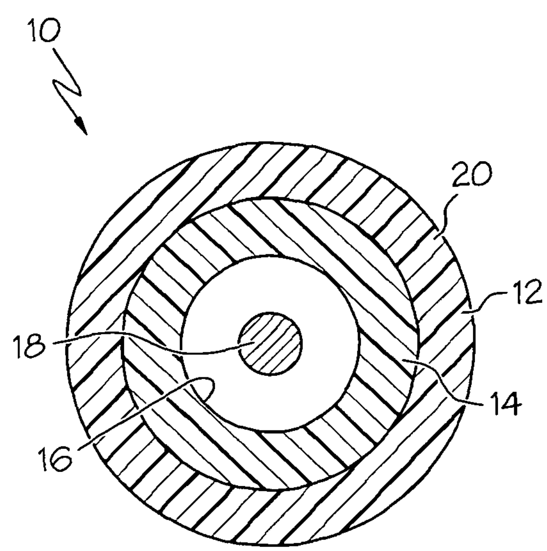

FIG. 11 is a cross section of the catheter tip of the catheter in FIG. 2 at line 2-2 with a circumferential band of electroactive polymer in the outer surface section of the catheter tip.

Figure 12A:
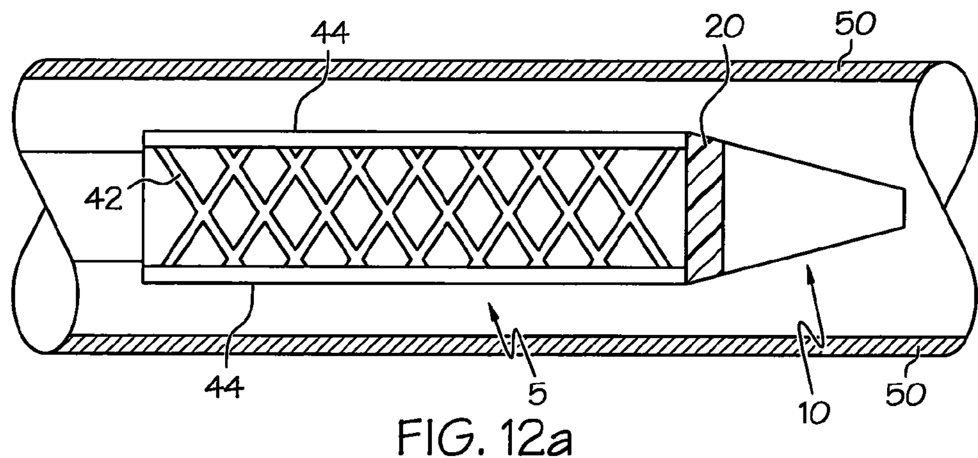

FIG. 12*a* shows a catheter assembly comprising an external sheath covering a self-expanding stent and a catheter tip with a circumferential band of electroactive polymer positioned in the proximal end region.

Figure 12B:
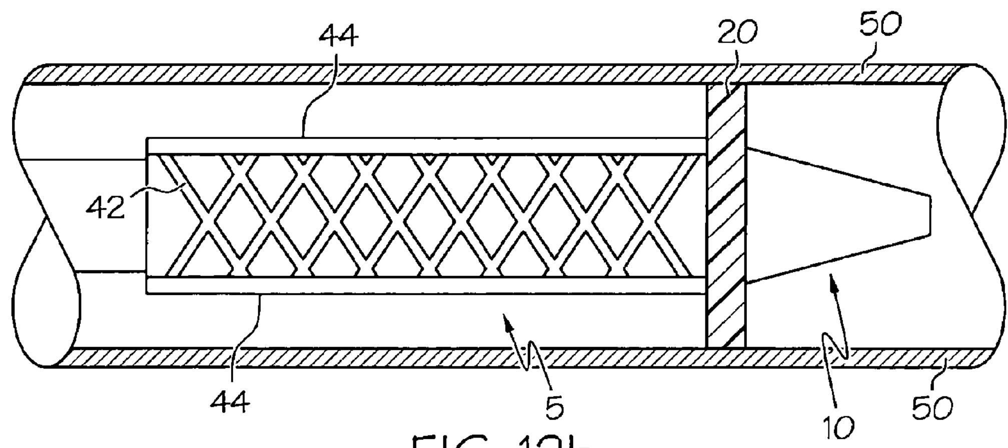

FIG. 12*b* shows the catheter assembly of FIG. 12*a* with the circumferential band of electroactive polymer in an actuated state prior to the withdrawal of the external sheath.

Figure 12C:
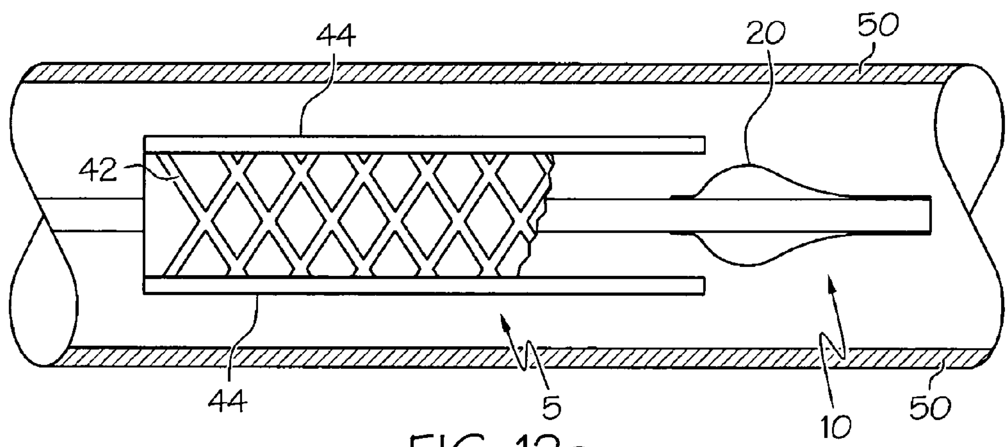

FIG. 12*c* shows a catheter assembly comprising an external sheath covering a self-expanding stent; a cut out of the self-expanding stent shows a sheath of electroactive polymer surrounding the catheter tip.

Figure 12D:
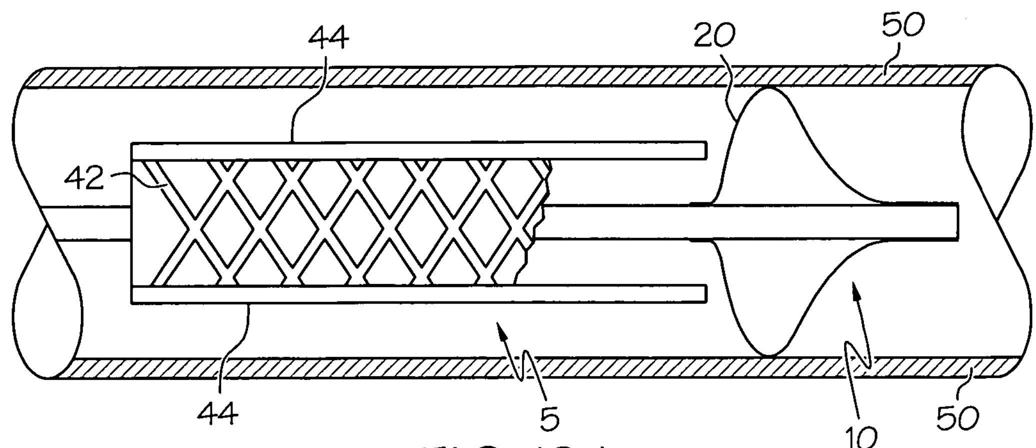

FIG. 12*d* shows the catheter assembly of FIG. 12*c* with the electroactive polymer in an actuated state prior to the withdrawal of the external sheath.

Figure 12E:
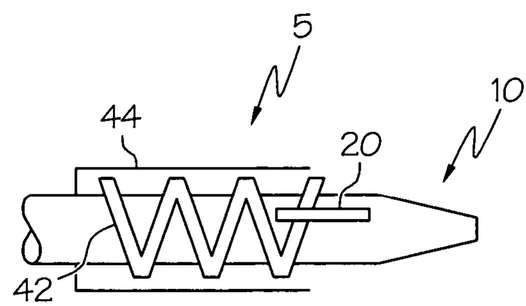

FIG. 12*e* shows a catheter assembly comprising an external sheath covering a self-expanding stent, the distal end of the self-expanding stent tethered to the catheter by at least one section of electroactive polymer.

Figure 12F:
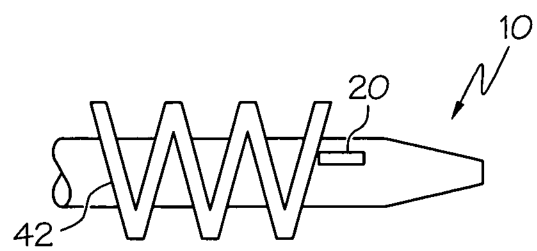

FIG. 12*f* shows the catheter assembly of FIG. 12*e* with the at least one section of electroactive polymer in an actuated state thereby releasing the distal end of the self-expanding stent from the catheter after the sheath has been withdrawn.

Figure 12G:
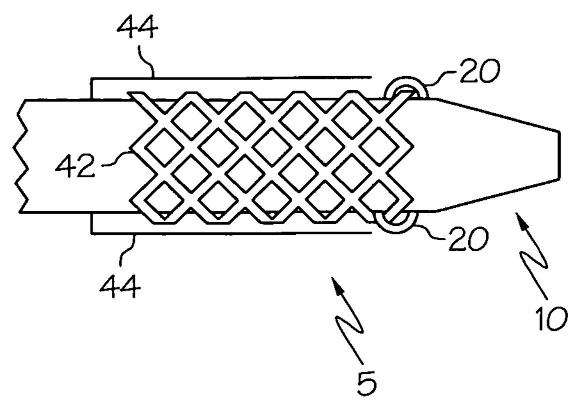

FIG. 12*g* shows a catheter assembly comprising an external sheath covering a self-expanding stent, a plurality of sections of electroactive polymer holding the distal end of the self-expanding stent in position on the catheter.

Figure 12H:
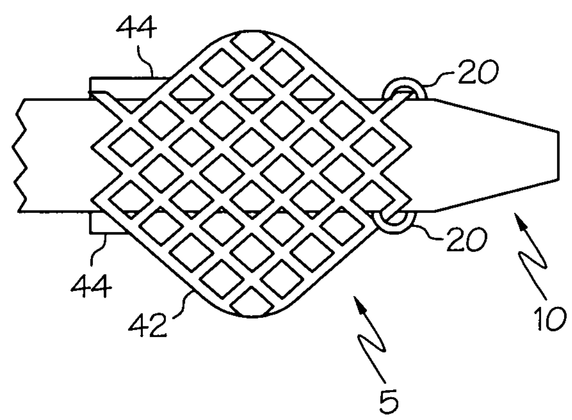

FIG. 12*h* shows the catheter assembly of FIG. 12*g* with the sheath partially withdrawn.

Figure 12I:
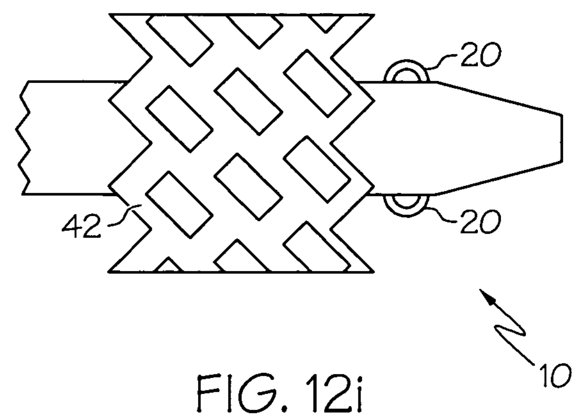

FIG. 12*i* shows the catheter assembly of FIG. 12*g* with the sheath completely withdrawn and the plurality of sections of electroactive polymer in an actuated state, thereby releasing the distal end of the self-expanding stent from the catheter.

Figure 13:
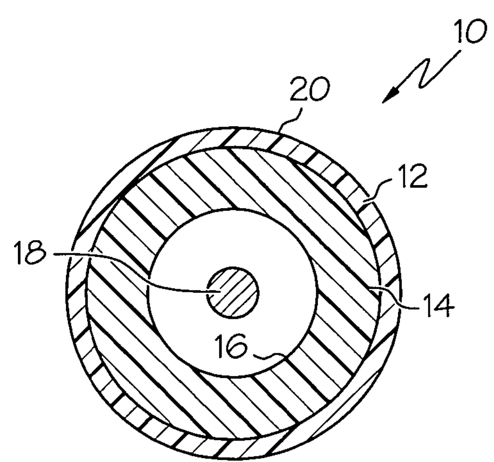

FIG. 13 shows the cross section of FIG. 11 with the electroactive polymer in an actuated state, where the electroactive polymer volumetrically contracts when actuated.

Figure 14B:
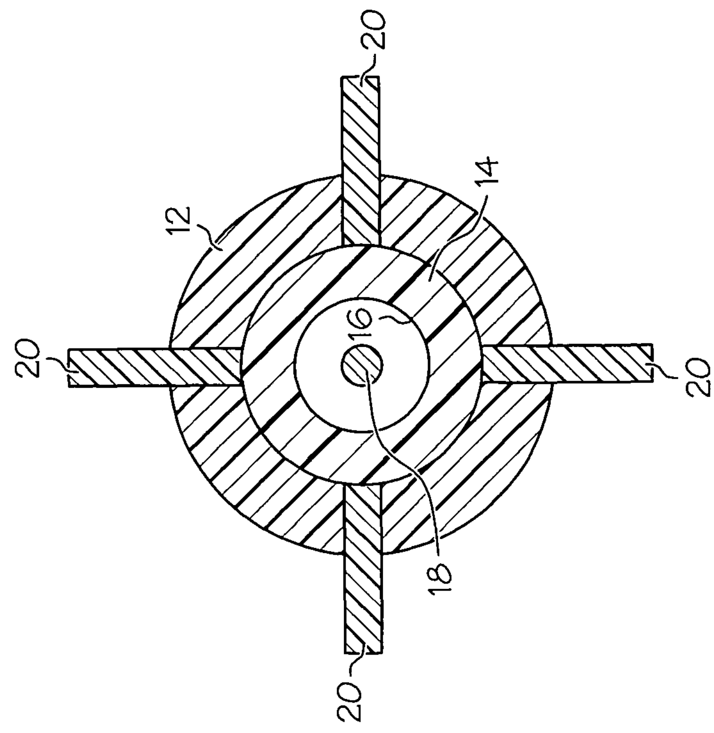
Figure 14A:
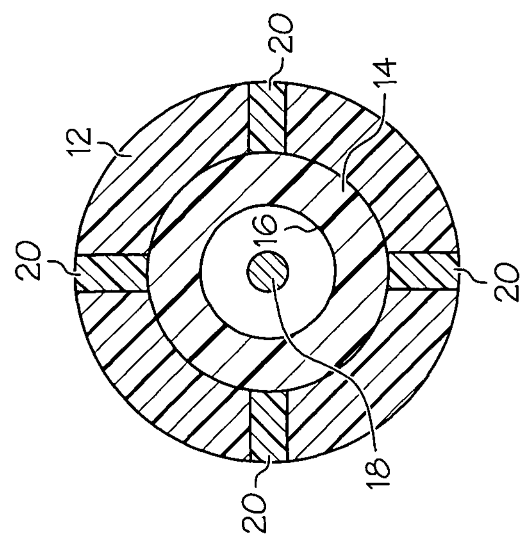

FIG. 14*a* is a cross section of the catheter tip of the catheter in FIG. 2 at line 2-2 with four longitudinal sections of electroactive polymer in the outer surface section of the catheter tip.

FIG. 14*b* depicts the catheter tip of FIG. 14*a* with the four longitudinal sections of electroactive polymer in an actuated state.

Figure 15B:
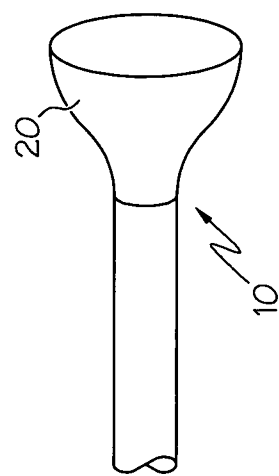
Figure 15A:
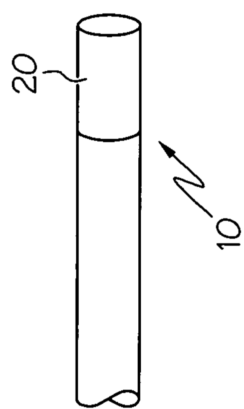

FIG. 15*a* is a side view of the catheter tip with at least one circumferential band of electroactive polymer at the distal end region of the catheter tip.

FIG. 15*b* is a side view of the catheter tip of FIG. 15*a* with the at least one circumferential band of electroactive polymer in an actuated state.

Figure 16A:
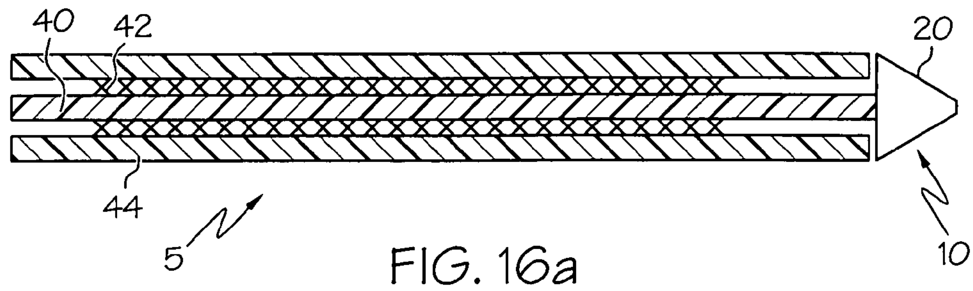

FIG. 16*a* is a longitudinal cross section of a catheter assembly with a catheter tip manufactured with EAP that is integrated with the inner shaft, and a self-expanding stent covered by an exterior sheath.

Figure 16B:
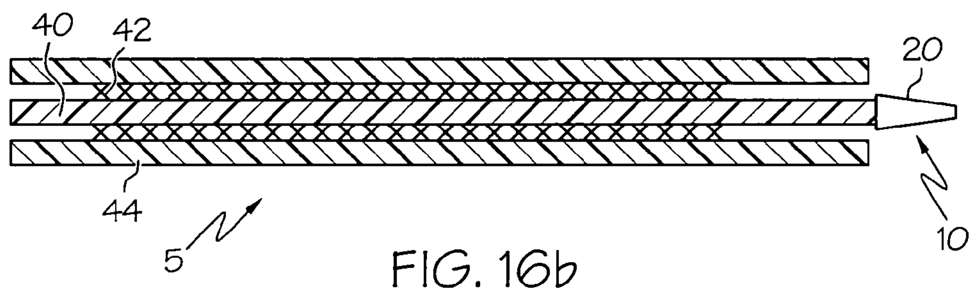

FIG. 16*b* is a longitudinal cross section of the catheter assembly of FIG. 16*a* with the EAP catheter tip in an actuated state.

Figure 17A:
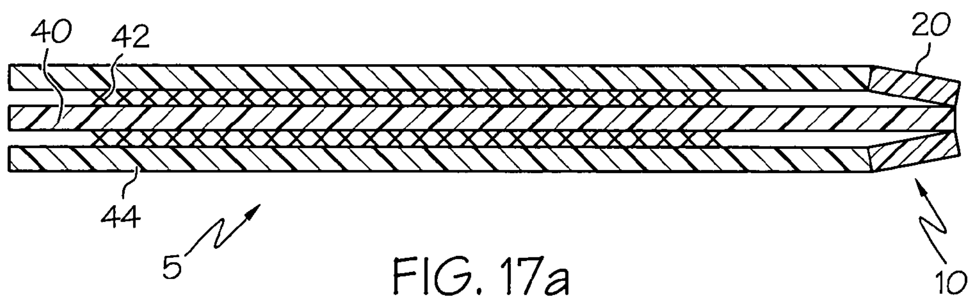

FIG. 17*a* is a longitudinal cross section of a catheter assembly with a catheter tip manufactured from EAP that is integrated with an exterior sheath which covers a self-expanding stent that is surrounding an inner shaft.

Figure 17B:
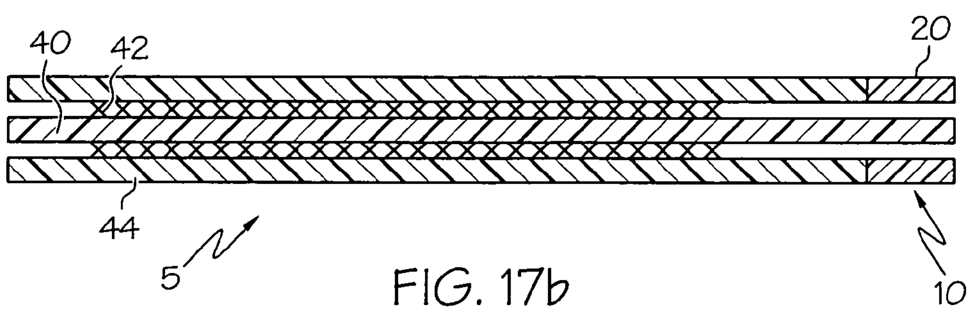

FIG. 17*b* is a longitudinal cross section of the catheter tip of FIG. 17*a* with the EAP catheter tip in an actuated state.

Figure 18:
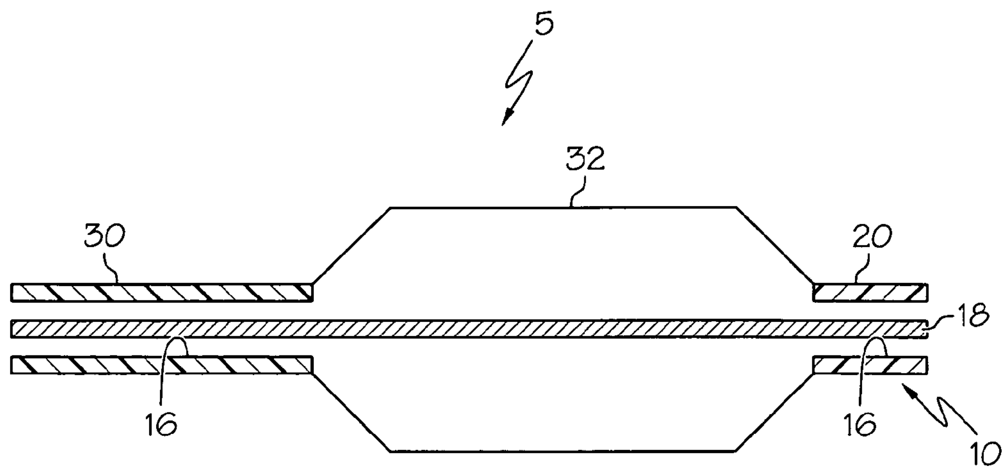

FIG. 18 is a longitudinal cross section of a balloon catheter having a tip with EAP, the balloon catheter lacking an inner shaft.

Figure 19:
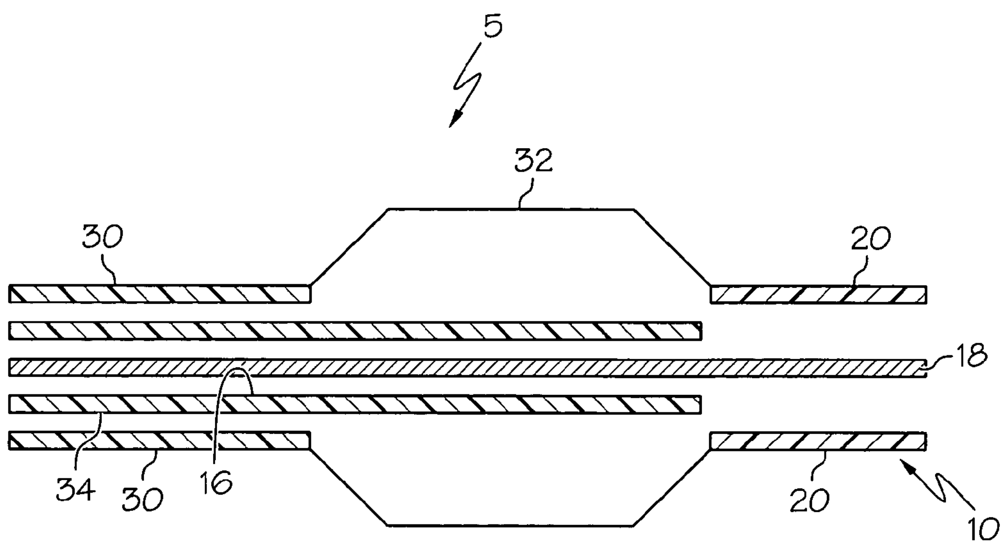

FIG. 19 is a longitudinal cross section of the balloon catheter in FIG. 18 with a slidable inner shaft.

Figure 20:
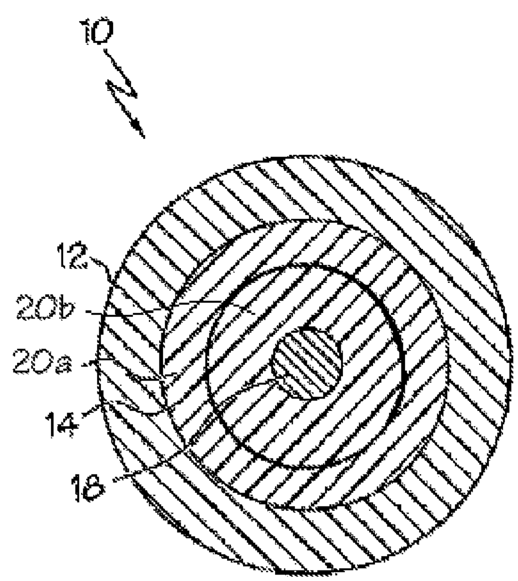

FIG. 20 is a cross-sectional view of two layers of EAP, each layer in an actuated state, engaging the guide wire.

DETAILED DESCRIPTION OF THE INVENTION

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

EAP has been discovered to be useful in a number of applications related to the design of catheter tips. EAPs have the ability to change shape upon actuation or deactuation.

Figure 1C:
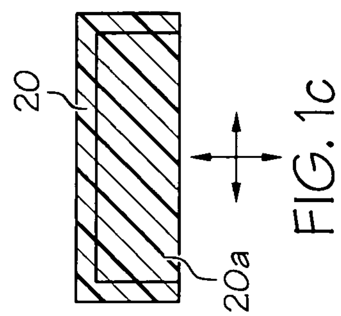
Figure 1B:
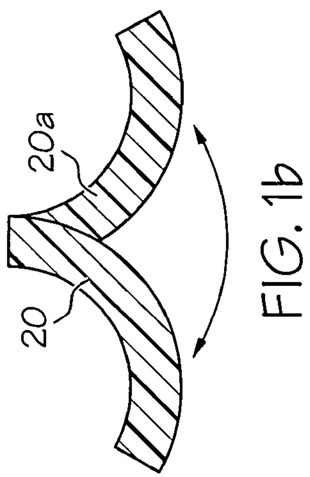
Figure 1A:
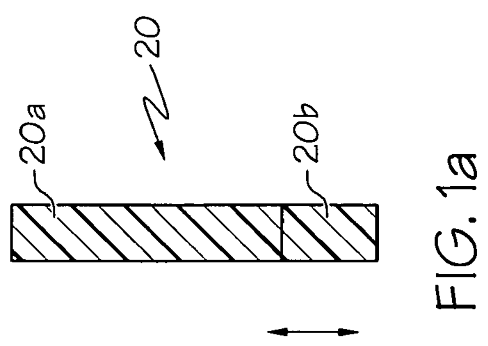

FIGS. 1*a-c* depict different ways EAP 20 can behave when actuated. FIG. 1*a* depicts how EAP 20 can increase or decrease its linear length. When EAP 20*a* is actuated, the linear length increases, the additional length denoted by portion 20*b*. The EAP may also be configured so that it decreases in length upon actuation. FIG. 1*b* shows how EAP 20 can bend when actuated with 20*a* denoting the EAP 20 prior to deformation and 20*b* denoting the EAP 20 after deformation. Alternatively, EAP can change from a straight configuration to a bent configuration or vice-versa upon actuation. FIG. 1*c* depicts how EAP 20 can increase or decrease its bulk or size (volumetrically expand or contract) when actuated. When EAP 20*a* is actuated and increases its bulk or size, it goes from an initial size of 20*a* to an actuated size of 20. When EAP 20 is actuated and decreases its bulk or size, it goes from an initial size of 20 to an actuated size of 20*a*.

In one embodiment of the invention, the spatial configuration of a catheter tip within the vicinity of a section of EAP changes when the section of EAP is actuated or deactuated. The EAP may be provided such that the thickness of the catheter tip shaft can change, either increasing or decreasing from an initial thickness. Thus, the catheter tip shaft has a non-actuated thickness when the section of EAP is in a non-actuated state and the catheter tip shaft has an actuated thickness when the section of EAP is in an actuated state. The non-actuated thickness is different from the actuated thickness. A second indicator of a change in spatial configuration is that the overall diameter of the catheter tip can change, either increasing or decreasing from an initial diameter, a non-actuated tip diameter, to an actuated tip diameter. Another indication of the change in spatial configuration is that the diameter of the guide wire lumen may change, either increasing or decreasing from an initial diameter, a non-actuated lumen diameter, to an actuated lumen diameter.

FIG. 2 shows a catheter 5 with a catheter tip 10 and a guide wire 18. The catheter tip can be given the desired shape using any generally suitable technique or construction, depending upon the materials used to make the tip. In at least one embodiment, the catheter tip is shaped through molding, thermoforming or thermal reforming, and the like. The catheter tip can be engaged to the shaft using any generally suitable technique or construction. In at least one embodiment, the tip can be heat welded or bonded to the distal portion of shaft. In at least one embodiment, the tip and the shaft are manufactured as one piece.

FIG. 3 shows a cross section of FIG. 2 at line 2-2 in which the catheter has been provided with an inventive catheter tip. The catheter tip 10 has an outer surface section 12 and an inner surface section 14 which form the shaft of the catheter tip 10. The interior surface of the catheter tip 10 defines a guide wire lumen 16. The guide wire lumen 16 has a non-actuated lumen diameter and an actuated lumen diameter. The non-actuated lumen diameter is different from the actuated lumen diameter. Optionally, a guide wire 18 extends within the guide wire lumen 16. The catheter tip 10 has at least one section of EAP 20. In at least one embodiment, the EAP is engaged to the tip after the tip has been formed. In the embodiment shown in FIG. 3, the section of EAP 20 is circumferential and comprises the entire inner surface section 14 of the catheter tip 10. In at least one embodiment, the section of EAP 20 comprises a portion of the inner surface section 14.

In at least one embodiment, shown in FIG. 4, the catheter tip 10 has a plurality of sections of EAP 20. It is also within the scope of the invention to have three, four, five, six, seven, or more sections of EAP. Each section of EAP 20 forms a circumferential band that forms a part of the shaft of the catheter tip 10. In one embodiment, each section of EAP forms a part of the inner surface section 14 of the catheter tip 10. In a non-actuated state, each band of EAP is substantially flush with the interior of the catheter tip. Each band of EAP 20 may be configured to volumetrically expand inward upon actuation to lock onto a different size guide wire. The engagement of the EAP with the guide wire would allow the physician to increase the push of the catheter. The physician can actuate the band of EAP which is sized to the guide wire being used. Because there is a plurality of EAP bands, the physician can choose to use one of several different sized guide wires with a single catheter tip and actuate the band of EAP that corresponds to the guide wire chosen.

In at least one embodiment, the catheter tip has a plurality of section of EAP which form circumferential layers of the inner surface section 14. It is also within the scope of the invention to have three, four, five, six, seven, or more circumferential layers. Each layer of EAP can be separately actuated. When actuated, each layer of EAP 20 volumetrically expands inward causing the size of the lumen to become progressively smaller as each layer of EAP is actuated. Desirably, the catheter tip 10 engages the guide wire 18 when the appropriate number of layer of EAP 20 is in an actuated state. As shown in FIG. 20, the inner surface section 14 has two circumferential layers of EAP 20*a*, 20*b*. Each layer 20*a*, 20*b* is in an actuated state so that the inner surface section 14 is engaged to the guide wire 18. Note that the layers of EAP 20 are radially adjacent one another so that the expansion of each layer inward causes the size of the lumen to become progressively smaller. The number of layers of EAP that need to be actuated will depend upon the size of the guide wire being used. This embodiment can allow the physician to use one catheter tip with a variety of guide wires. This embodiment can allow the physician to increase the push of the catheter.

In at least one embodiment, the catheter tip has a plurality of sections of EAP which form circumferential layers of the inner surface section. It is also within the scope of the invention to have three, four, five, six, seven, or more circumferential layers. Each layer of EAP can be separately actuated. When actuated, each layer of EAP volumetrically contracts causing the size of the lumen to become progressively larger as each layer of EAP is actuated. The number of layers of EAP that need to be actuated will depend upon the size of the guide wire being used. This embodiment will allow the physician to use one catheter tip with guide wires of different sizes.

In at least one embodiment, the section of EAP 20 in the inner surface section 14 may be configured to volumetrically expand inward when in an actuated state. This can be seen in FIG. 5, which is the cross-section of FIG. 3 with the EAP 20 in an actuated state. In this embodiment, the actuated lumen diameter is smaller than the non-actuated lumen diameter. In one embodiment, the catheter tip 10 engages the guide wire 18 when the EAP 20 is in an actuated state. In use, when the catheter tip 10 engages the guide wire 18, the catheter will become laterally stiffer which will cause the catheter to have better push which will allow the catheter to cross difficult anatomy or lesions. The engagement of the EAP with the guide wire will cause the guide wire 18 to behave in a manner similar to a fixed wire. In one embodiment, the section of EAP 20 is a circumferential band that forms a portion of the inner surface section 14. In a non-actuated state, the band of EAP 20 is substantially flush with the interior of the catheter tip 10.

In one embodiment, the section of EAP in the inner surface section may be configured to volumetrically contract when in an actuated state. In this embodiment, the actuated lumen diameter is larger than the non-actuated lumen diameter. If the guide wire locks up, the section of EAP can be actuated thereby keeping enlarging the size of the port. The EAP can be maintained in an actuated state during tracking and de-actuated when the catheter assembly is in the proper position within the body lumen.

In another embodiment, the section of EAP 20 in the inner surface section 14 contracts when in an actuated state. In this embodiment, the actuated lumen diameter is larger than the non-actuated lumen diameter.

FIG. 6 shows the cross section of FIG. 3 with the circumferential band of EAP 20 in an actuated state. In this embodiment, the circumferential band of EAP 20 volumetrically contracts when actuated. Thus, the actuated lumen diameter is larger than the non-actuated lumen diameter. The circumferential band of EAP can be actuated while the guide wire 18 is being loaded or when guide wire 18 movement issues are encountered.

FIGS. 7*a, b* and *c* depict a longitudinal cross-section of a balloon catheter 5 with a catheter tip 10 with a circumferential band of EAP 20 located in the inner surface section 14 of the catheter tip 10. The circumferential band of EAP 20 allows guide wires 18 of different sizes to be used with a single catheter tip 10. The catheter tip 10 may be manufactured separately from the catheter 5 and engaged to the catheter 5 or, the catheter 5 and the catheter tip 10 may be manufactured as one piece. The catheter tip 10 has a section of EAP 20 which will allow the catheter tip 10 to be used with multiple sized guide wires 18.

As shown in FIG. 7*b*, the circumferential band of EAP 20 in a non-actuated state can accommodate a large sized guide wire 18, for example, but not limited to, a 0.035 guide wire. If a smaller size guide wire 18 is used, for example, but not limited to, a 0.018 or 0.014 guide wire, the section of EAP 20 can be actuated. As shown in FIG. 7*c*, actuation of the section of EAP 20 will cause the section of EAP 20 to volumetrically expand and will cause the size of the guide wire lumen 16 to decrease. This will give the physician the flexibility to use the appropriate sized guide wire with one size catheter tip.

A catheter having a tip with an inner lumen with a diameter that may be varied may facilitate loading a guide wire and delivery of the catheter to a desired bodily location is also within the scope of the invention. Thus, in one embodiment of the invention, the catheter tip may be provided with EAP along at least a portion of the inner lumen. The EAP may be switched between an enlarged state and a non-enlarged state. In the non-enlarged state of the EAP, the inner lumen has an enlarged diameter which facilitates loading the catheter on the guide wire. When the EAP is in an enlarged state, the inner lumen has improved trackability and cross-ability because the lumen diameter has decreased. FIG. 8 is a cross-section of FIG. 3 with the EAP 20 in an actuated state. In this embodiment, the EAP 20 volumetrically expands when actuated and causes the diameter of the guide wire lumen 16 to decrease in size. Actuation of the EAP 20 will enhance the trackability and cross-ability of the catheter system.

In at least one embodiment, the balloon catheter assembly has a lockable positioning system. The catheter tip 10 has at least one section of EAP 20. In this embodiment, the at least one section of EAP 20 is a circumferential band that forms the shaft of the catheter tip 10. When actuated the EAP 20 volumetrically expands, causing the guide wire lumen 16 to decrease in size so that the guide wire lumen 16 becomes occluded. If a guide wire 18 is within the guide wire lumen 16, when the EAP 20 is actuated, the EAP 20 engages the guide wire 18 thereby occluding the guide wire lumen 16. Desirably, actuation of the EAP causes the distal end of the balloon catheter to become occluded and allows the balloon to inflate since the inflation media will not escape through the distal end of the balloon catheter. In one embodiment, the circumferential band of EAP forms the inner section of the catheter tip.

In at least one embodiment, shown in FIG. 9 the inner surface section 14 of the catheter tip 10 has a circumferential coil of EAP 20. The circumferential coil of EAP 20 can either volumetrically expand or volumetrically contract when actuated. If the circumferential coil of EAP 20 volumetrically expands when actuated, the size of the guide wire lumen 16 increases thereby allowing for greater movement of the guide wire 18. If the circumferential coil of EAP 20 volumetrically contracts when actuated, the size of the guide wire lumen 16 decreases. In at least one embodiment, the circumferential coil of EAP 20 engages the guide wire 18 when the EAP 20 is actuated, thereby causing the guide wire to behave similarly to a fixed wire.

In at least one embodiment, shown in FIGS. 10*a* and 10*b*, the EAP in the catheter tip affects the stiffness of the catheter tip allowing for either CTO or varying vessel tortuousness. FIG. 10*a* shows the catheter assembly 5 with a stent 42 and the inventive catheter tip 10 as it is guided through the vessel by a guide wire 18. FIG. 10*b* is an enlargement of a portion of the catheter tip 10 of the catheter assembly 5 of FIG. 10*a*, positioned next to an occlusion of the blood vessel, as it looks in an actuated state. The catheter tip 10 has two regions of EAP 20A and 20B, region A, and region B. The dashed line on the catheter tip in FIG. 10*b* shows the relative positions of these two regions, with region A positioned proximally to region B. Region A can be actuated and de-actuated independently of region B. The EAP 20A in region A gains more mass and stiffness in an actuated state than does the EAP 20B in region B in either an actuated or de-actuated state.

In one embodiment, region A of the catheter tip is manufactured of EAP while region B of the catheter tip is manufactured of another material. Examples of suitable materials for region B of the catheter tip include, but are not limited to, polymers such as polyoxymethylene (POM), polybutylene terephthalate (PBT), polyether block ester, polyether block amide (PEBA), fluorinated ethylene propylene (FEP), polyethylene (PE), polypropylene (PP), polyvinylchloride (PVC), polyurethane, polytetrafluoroethylene (PTFE), polyether-ether ketone (PEEK), polyimide, polyamide, polyphenylene sulfide (PPS), polyphenylene oxide (PPO), polysufone, nylon, perfluoro (propyl vinyl ether) (PFA), polyether-ester, polymer/metal composites, etc., or mixtures, blends or combinations thereof. In this embodiment, the EAP 20A in region A gains more mass and stiffness in an actuated state than the material used to manufacture region B of the catheter tip.

FIG. 11 depicts a cross section of FIG. 2 at line 2-2 in which the catheter has been provided with another inventive catheter tip. The catheter tip 10 has an outer surface section 12 and an inner surface section 14. The interior surface of the catheter tip 10 defines a guide wire lumen 16. Optionally, a guide wire 18 extends within the guide wire lumen 16. The catheter tip 10 has at least one section of EAP 20. In the embodiment depicted in FIG. 11, the section of EAP 20 is circumferential and comprises the entire outer surface section 12 of the catheter tip 10. The catheter tip 10 has a non-actuated tip diameter and an actuated tip diameter. The non-actuated tip diameter is different from the actuated tip diameter. In at least one embodiment, the section EAP 20 comprises a portion of the outer surface section 12.

A catheter with an inventive catheter tip is depicted in FIGS. 12*a, b, c* and *d*. In FIG. 12*a*, the catheter assembly 5 is shown in a body lumen. The catheter assembly 5 comprises an external sheath 44 which is surrounding a self expandable stent 42. The catheter tip 10 of the catheter assembly 5 has a circumferential band of EAP 20 at the proximal end region of the catheter tip 10. The circumferential band of EAP 20 is in a non-actuated state.

FIG. 12*b* depicts the catheter assembly of FIG. 12*a* with the circumferential band of EAP 20 in an actuated state. Because the circumferential band of EAP 20 in the outer surface section volumetrically expands when in an actuated state, the actuated tip diameter in the vicinity of the band of EAP 20 is larger than the non-actuated tip diameter in the vicinity of the band of EAP 20. In at least one embodiment, the circumferential band of EAP 20 engages the lumen wall. Thus, the expansion properties of the EAP 20 containing catheter tip 10 may also be used to temporarily anchor the catheter tip 10 of the catheter 5 in the vessel.

The circumferential band of EAP 20 is actuated before the exterior sheath 44 covering the self-expanding stent 42 is withdrawn. Because the circumferential band of EAP 20 engages the lumen wall, the self-expanding stent 42 is unable to move past the catheter tip 10 as the exterior sheath 44 is withdrawn from the stent 42. Thus, this could be used to prevent a self-expanding stent 42 that is being deployed from jumping past the catheter tip 10. Once the self-expanding stent 42 has been deployed, the circumferential band of EAP 20 can be de-actuated so that the catheter assembly 5 can be withdrawn from the lumen while the stent 42 remains in the desired location within the lumen.

FIGS. 12*c* and 12*d* depict another embodiment that can be used to prevent a self-expanding stent 42 from jumping past the catheter tip 10 during deployment in a vessel 50. A portion of the self-expanding stent 42 in FIGS. 12*c* and 12*d* is cut out in order to show the catheter tip 10. A sheath of EAP 20 is engaged to the catheter tip 10.

FIG. 12*d* shows the sheath of EAP 20 in an actuated state. When the catheter assembly 5 is in the desired position within the vasculature, the sheath of EAP 20 can be actuated. Actuation of the sheath of EAP 20 causes the EAP 20 to volumetrically contract which causes the diameter of the catheter tip 10 to increase. The increase in the diameter of the catheter tip 10 is sufficient to prevent the self-expanding stent 42 from moving past the catheter tip 10 when the external sheath 44 is withdrawn. In one embodiment, actuation of the sheath of EAP engages the catheter tip with the vessel wall 50.

Additional embodiments that prevent a self-expanding stent from jumping past the catheter tip during deployment are shown in FIGS. 12*e-f* and 12*g-i*. FIG. 12*e* shows a catheter assembly 5 with an external sheath 44 covering a self-expanding stent 44 which has at least one section of EAP 20 extending over a portion of the distal end of the stent 44. It is also within the scope of the invention to have three, four, five, six, seven, or more sections of EAP 20. Once the external sheath 44 is withdrawn and the self-expanding stent 42 has expanded, the at least one section of EAP 20 can be actuated. When actuated, the at least one section of EAP 20 decreases in length thereby releasing the distal end of the stent 42. FIG. 12*f* shows the catheter assembly 5 of FIG. 12*e* with external sheath 44 retracted, the self-expanding stent 42 fully deployed and the at least one section of EAP 20 in the shorter actuated length. In one embodiment, the at least one section of EAP 20 is engaged to the catheter assembly 5 after the self-expanding stent 42 has been engaged to the stent loading area of the catheter assembly 5.

FIGS. 12*g-i* show an alternative means to tether the distal end of a self-expanding stent 42 to a catheter 5 in order to prevent undesired distal movement of the stent 42 past the catheter tip 10 during deployment. In this embodiment, an external sheath 44 covers a self-expanding stent 42. At least one section of EAP 20 tethers the distal end of the stent 42 to the catheter 5. It is also within the scope of the invention to have three, four, five, six, seven, or more sections of EAP 20. The at least one section of EAP 20 is bent over a stent band at the distal end of the stent 42. FIG. 12*h* shows the catheter assembly of FIG. 12*g* with the external sheath 44 partially withdrawn from the self-expanding stent 42. At this point of stent deployment, the middle section of the stent 42 expands outward while the proximal end of the stent 42 remains close to the catheter 5 due to the sheath 44 and the distal end of the stent 42 remains engaged to the catheter 5 due to the at least one section of EAP 20. FIG. 12*i* shows the catheter assembly 5 with the stent 42 fully deployed and the at least one section of EAP 20 in an actuated state. In an actuated state, the EAP 20 goes from a bent configuration to a bent configuration, thereby releasing the distal end of the stent 42. After the stent 42 is fully deployed, the catheter assembly 5 can be removed without further manipulation of the at least one section of EAP 20.

In one embodiment, the at least one section of EAP 20 goes from a bent configuration to a straight configuration when actuated, thereby releasing the distal end of the stent 42. It is also within the scope of the invention to have three, four, five, six, seven, or more sections of EAP 20. In this embodiment, since the at least one section of EAP 20 extends perpendicularly from the outer surface of the catheter 5 after it is actuated, the at least one section of EAP 20 must be deactuated before the catheter assembly 5 can be removed. The at least one section of EAP 20 resumes a bent configuration once it is de-actuated and the catheter assembly S can be removed from the lumen.

FIG. 13*a* depicts an inventive catheter tip 10 with four longitudinal sections of EAP 20 in the outer surface section 12. It is also within the scope of the invention to have two, three, five, six or more longitudinal sections of EAP. When actuated, the sections of EAP 20 volumetrically expand, as shown in FIG. 13*b*. In use, the catheter tip 10 can be engaged to the wall of the vessel 50, thereby stabilizing and providing good support for the catheter assembly 5, while allowing the flow of blood past the catheter tip 10. In one embodiment, the longitudinal sections of EAP 20 are engaged to the catheter tip 10 after the catheter tip 10 was formed. In one embodiment, the longitudinal sections of EAP 20 form a portion of the catheter tip shaft.

In another embodiment, shown in FIGS. 14*a* and 14*b*, the inventive catheter tip 10 has at least one circumferential section of EAP 20 positioned in the outer surface section 12 at the distal end region of the catheter tip 10. When actuated, the section(s) of EAP 20 differentially expand thereby causing the distal end of the catheter tip 10 to flare. This will allow the physician to guide the guide wire back into the catheter assembly. In one embodiment, the sections of EAP 20 are applied to the distal end region of the catheter tip 10 after the catheter tip 10 was formed. In one embodiment, the sections of EAP 20 form the shaft of the distal end region of the catheter tip 10.

In another embodiment, shown in FIG. 15, the section of EAP 20 in the outer surface section 12 volumetrically contracts when in an actuated state. Thus, the actuated tip diameter is smaller than the non-actuated tip diameter and the lumen diameter remains constant. This could result in improved crossing characteristics of the catheter. In at least one embodiment, the lumen diameter remains constant when the section of EAP 20 in the outer surface section 12 is actuated. In one embodiment, the section of EAP 20 is applied to the catheter tip 10 after the catheter tip 10 was formed.

In at least one embodiment, not shown, the distal end region of the catheter tip has a plurality of longitudinal sections of EAP about the circumference of the catheter tip. When actuated the length of the plurality of sections of EAP changes, either increasing or decreasing in length. In one embodiment, the entire circumference of the catheter tip is made of longitudinal sections of EAP. It is also within the scope of the invention to have four, five, six, seven, eight, nine, ten or more longitudinal sections of EAP about the circumference of the catheter tip. In one embodiment, the plurality of longitudinal sections of EAP are positioned within the outer surface section of the catheter tip. In one embodiment, the plurality of longitudinal sections of EAP form the shaft of the catheter tip.

In one embodiment, the plurality of sections of EAP increase in length when actuated. Increasing the length of the catheter tip may facilitate tracking of the catheter assembly through the anatomy.

In one embodiment, the plurality of sections EAP decrease in length when actuated. Decreasing the length of the catheter tip may allow for the placement of the catheter where distal place is limited, for example, but not limited to, when using a distal protection device.

The inventive catheter tip can be manufactured in several ways. In at least one embodiment, the catheter tip and catheter shaft are manufactured as one unit.

As shown in FIG. 16*a*, a catheter tip 10 manufactured of EAP 20 is engaged to the inner shaft 40 of a self-expanding stent delivery system. In one embodiment, the catheter tip 10 and inner shaft 40 are manufactured as one unit. When the EAP 20 is in a non-actuated state, there is a smooth transition from the outer diameter of the exterior sheath 44 to the guide wire lumen 16. FIG. 16*b* depicts the EAP 20 in the catheter tip 10 in an actuated state. When the EAP 20 is in an actuated state, the diameter of the catheter tip 10 decreases because the EAP 20 volumetrically contracts. The EAP 20 would be actuated to allow for the manufacture of the stent delivery system and during deployment of the self expanding stent 42 to allow the inner shaft 40 to be withdrawn away from the stent 42.

FIG. 17*a* depicts a catheter tip 10 manufactured of EAP 20 attached to an exterior sheath 44 covering a self-expanding stent 42. In at least one embodiment, a catheter tip 10 manufactured of EAP 20 is integrated with the exterior sheath 44. The catheter tip 10 in FIG. 17*a* is in a collapsed state. The catheter tip 10 in a collapsed state provides a smooth transition to the guide wire lumen 16 as well as provide good trackability of the catheter 5.

In FIG. 17*b*, the catheter tip 10 is in a non-collapsed state due to actuation of the EAP 20. The EAP 20 goes from a bent configuration to a linear configuration when actuated. The EAP 20 can be actuated during the manufacture of the delivery system as well as during deployment of the stent 42.

In at least one embodiment, a catheter assembly with the inventive catheter tip is used to deploy an implantable device. In at least one embodiment, a catheter assembly with the inventive catheter tip is used to deploy a stent.

In another embodiment, shown in FIG. 18, a balloon catheter 5 has a tip 10 with EAP 20. The catheter 5 has a shaft 30, a balloon 32 and a tip 10 with a section of EAP 20. The balloon 32 is bonded directly to the tip 10 at the distal end and is bonded directly to the shaft 30 at the proximal end. The interior surface of the shaft 30 forms a guide wire lumen 16 which may house a guide wire 18. The guide wire 18 may be loaded into the balloon catheter 5 with a hollow crimping mandrel. The mandrel is left inside the balloon catheter until the guide wire has been inserted. The section of EAP 20 in the catheter tip 10 is a circumferential band that forms the wall of the catheter tip 10. When actuated the EAP 20 volumetrically expands, causing the guide wire lumen 16 to decrease in size so that the guide wire lumen 16 becomes occluded. If a guide wire 18 is within the guide wire lumen 16, when the EAP 20 is actuated, the EAP 20 engages the guide wire 18 thereby occluding the guide wire lumen 16. Desirably, actuation of the EAP causes the distal end of the balloon catheter to become occluded and allows the balloon to inflate since the inflation media will not escape through the distal end of the balloon catheter. In at least one embodiment, the circumferential band of EAP forms the inner section of the catheter tip. In one embodiment, the circumferential band of EAP forms the shaft of the catheter tip.

In at least one embodiment, shown in FIG. 19, the balloon catheter has a slidable inner shaft 34 which is not engaged to the shaft 30, the balloon 32 or the catheter tip 10. The distal end of the slidable inner shaft 34 terminates at the proximal edge of the catheter tip 10. The slidable inner shaft 34 has an interior surface that defines a guide wire lumen 16. The slidable inner shaft 34 may be loaded into the balloon catheter 5 with a hollow crimping mandrel. In at least one embodiment, the slidable inner shaft is loaded into the balloon catheter by a monorail. The slidable inner shaft 34 is controlled by a manifold with a slide. When the slide is initially engaged, it would be at the distal end of is stroke and the slidable inner shaft 34 would be in place. When the mechanism is slid proximally, the inner shaft 34 disengages. By attaching the inner to sliding mechanism, the slidable inner shaft 34 would not be able to advance any further than the distal end of the shaft 30 or the proximal end of the catheter tip 10.

In one embodiment, the wall of the catheter tip 10 is thicker than the wall of the shaft 30. Desirably, this would prevent the slidable inner shaft from moving past the proximal edge of the catheter tip 10. In one embodiment, the slidable inner shaft 34 has a flared distal end such that the slidable inner shaft 34 cannot advance past the proximal end of the catheter tip 10. In one embodiment, the flared end is made by actuating a circumferential band of EAP which volumetrically expands when actuated.

The outer surface section 12 and the inner surface section 14 of the catheter tip 10, and the shaft 30 can be constructed from one material, two different materials or a blend of materials in addition to the section(s) of EAP 20. Examples of suitable materials for the catheter tip, the shaft and slidable inner shaft include, but are not limited to, polymers such as polyoxymethylene (POM), polybutylene terephthalate (PBT), polyether block ester, polyether block amide (PEBA), fluorinated ethylene propylene (FEP), polyethylene (PE), polypropylene (PP), polyvinylchloride (PVC), polyurethane, polytetrafluoroethylene (PTFE), polyether-ether ketone (PEEK), polyimide, polyamide, polyphenylene sulfide (PPS), polyphenylene oxide (PPO), polysufone, nylon, perfluoro (propyl vinyl ether) (PFA), polyether-ester, polymer/metal composites, etc., or mixtures, blends or combinations thereof.

In at least one embodiment the inner surface section 14 is constructed from a different material than the outer surface section 12. In at least one embodiment, the slidable inner shaft 34 is constructed from a different material than the shaft 30. Specifically, the inner surface section 14 or the slidable inner shaft 34 is made of a lubricious material, e.g. tetrafluoroethylene (PTFE), or a copolymer of tetrafluoroethylene with perfluoroalkyl vinyl ether (PFA) (more specifically, perfluoropropyl vinyl ether or perfluoromethyl vinyl ether), or the like.

The catheters of the present invention are actuated, at least in part, using EAP actuators. EAPs are characterized by their ability to change shape in response to electrical stimulation. EAPs include electric EAPs and ionic EAPs. Piezoelectric materials may also be employed but tend to undergo small deformation when voltage is applied.

Electric EAPs include ferroelectric polymers, dielectric EAPs, electrorestrictive polymers such as the electrorestrictive graft elastomers and electro-viscoelastic elastomers, and liquid crystal elastomer materials.

Ionic EAPs include ionic polymer gels, ionomeric polymer-metal composites, conductive polymers and carbon nanotubes. Upon application of a small voltage, ionic EAPs can bend significantly. Ionic EAPs also have a number of additional properties that make them attractive for use in the devices of the present invention, including the following: (a) they are lightweight, flexible, small and easily manufactured; (b) energy sources are available which are easy to control, and energy can be easily delivered to the EAPs; (c) small changes in potential (e.g., potential changes on the order of 1V) can be used to effect volume change in the EAPs; (d) they are relatively fast in actuation (e.g., full expansion/contraction in a few seconds); (e) EAP regions can be created using a variety of techniques, for example, electrodeposition; and (f) EAP regions can be patterned, for example, using photolithography, if desired. Conductive plastics may also be employed. Conductive plastics include common polymer materials which are almost exclusively thermoplastics that require the addition of conductive fillers such as powdered metals or carbon (usually carbon black or fiber). Ionic polymer gels are activated by chemical reactions and can become swollen upon a change from an acid to an alkaline environment.

Ionomeric polymer-metal composites can bend as a result of the mobility of cations in the polymer network. Suitable base polymers include perfluorosulfonate and perfluorocarboxylate.

Any of a variety of pi-conjugated polymers may be employed herein. Examples of suitable conductive polymers include, but are not limited to, polypyrroles, polyanilines, polythiophenes, polyethylenedioxythiophenes, poly(p-phenylenes), poly(p-phenylene vinylene)s, polysulfones, polypyridines, polyquinoxalines, polyanthraquinones, poly(N-vinylcarbazole)s and polyacetylenes, with the most common being polythiophenes, polyanilines, and polypyrroles. Some of the structures are shown below:

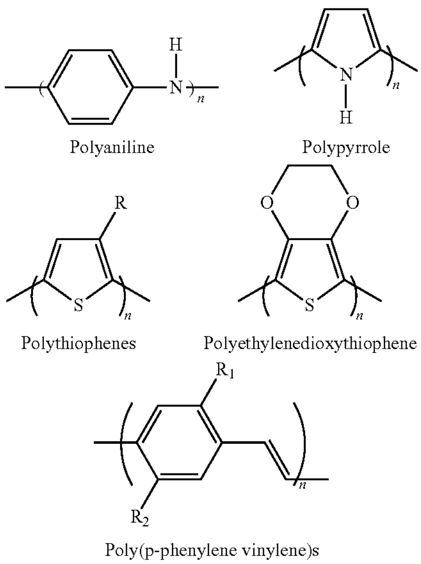

Polypyrrole, shown in more detail below, is one of the most stable of these polymers under physiological conditions:

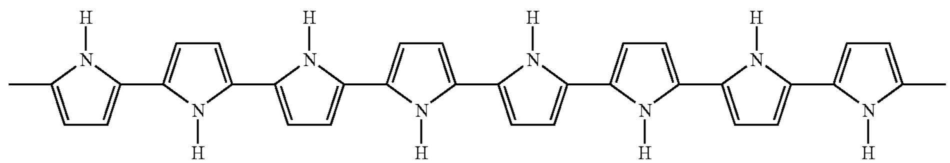

Essentially any electroactive polymer that exhibits contractile or expansile properties may be used in connection with the various active regions of the invention, including any of those listed above.

In some embodiments herein, the EAPs employed are ionic EAPs, more specifically, the ionic EAPs are conductive polymers that feature a conjugated backbone (they include a backbone that has an alternating series of single and double carbon-carbon bonds, and sometimes carbon-nitrogen bonds, i.e. π-conjugation) and have the ability to increase the electrical conductivity under oxidation or reduction. For polymers allows freedom of movement of electrons, therefore allowing the polymers to become conductive. The pi-conjugated polymers are converted into electrically conducting materials by oxidation (p-doping) or reduction (n-doping).

The volume of these polymers changes dramatically through redox reactions at corresponding electrodes through exchanges of ions with an electrolyte. The EAP-containing active region contracts of expands in response to the flow of ions out of, or into, the same. These exchanges occur with small applied voltages and voltage variation can be used to control actuation speeds.

The above list is intended for illustrative purposes only, and not as a limitation on the scope of the present invention.

The behavior of conjugated polymers is dramatically altered with the addition of charge transfer agents (dopants). These materials can be oxidized to a p-type doped material by doping with an anionic dopant species or reducible to a n-type doped material by doping with a cationic dopant species. Generally, polymers such as polypyrrole (PPy) are partially oxidized to produce p-doped materials:

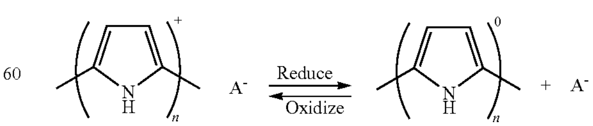

Dopants have an effect on this oxidation-reduction scenario and convert semi-conducting polymers to conducting versions close to metallic conductivity in many instances. Such oxidation and reduction are believed to lead to a charge imbalance that, in turn, results in a flow of ions into or out of the material. These ions typically enter/exit the material from/into an ionically conductive electrolyte medium associated with the EAP.

Dimensional or volumetric changes can be effectuated in certain polymers by the mass transfer of ions into or out of the polymer. This ion transfer is used to build conductive polymer actuators (volume change). For example, in some conductive polymers, expansion is believed to be due to ion insertion between chains, whereas in others inter-chain repulsion is believed to be the dominant effect. Regardless of the mechanism, the mass transfer of ions into and out of the material leads to an expansion or contraction of the polymer, delivering significant stresses (e.g., on the order of 1 MPa) and strains (e.g., on the order of 10%). These characteristics are ideal for construction of the devices of the present invention. As used herein, the expansion or the contraction of the active region of the device is generally referred to as "actuation."

The following elements are commonly utilized to bring about EAP actuation: (a) a source of electrical potential, (b) an active region, which comprises the EAP, (c) a counter electrode and (d) an electrolyte in contact with both the active region and the counter electrode.

The source of electrical potential for use in connection with the present invention can be quite simple, consisting, for example, of a dc battery and an on/off switch. Alternatively, more complex systems can be utilized. For example, an electrical link can be established with a microprocessor, allowing a complex set of control signals to be sent to the EAP-containing active region(s).

The electrolyte, which is in contact with at least a portion of the surface of the active region, allows for the flow of ions and thus acts as a source/sink for the ions. Any suitable electrolyte may be employed herein. The electrolyte may be, for example, a liquid, a gel, or a solid, so long as ion movement is permitted. Examples of suitable liquid electrolytes include, but are not limited to, an aqueous solution containing a salt, for example, a NaCl solution, a KCl solution, a sodium dodecylbenzene sulfonate solution, a phosphate buffered solution, physiological fluid, etc. Examples of suitable gel electrolytes include, but are not limited to, a salt-containing agar gel or polymethylmethacrylate (PMMA) gel. Solid electrolytes include ionic polymers different from the EAP and salt films.

The counter electrode may be formed from any suitable electrical conductor, for example, a conducting polymer, a conducting gel, or a metal, such as stainless steel, gold or platinum. At least a portion of the surface of the counter electrode is generally in contact with the electrolyte, in order to provide a return path for charge.

In one specific embodiment, the EAP employed is polypyrrole. Polypyrrole-containing active regions can be fabricated using a number of known techniques, for example, extrusion, casting, dip coating, spin coating, or electro-polymerization/deposition techniques. Such active regions can also be patterned, for example, using lithographic techniques, if desired.

As a specific example of a fabrication technique, polypyrrole can be galvanostatically deposited on a platinised substrate from a pyrrole monomer solution using the procedures described in D. Zhou et al., "Actuators for the Cochlear Implant," *Synthetic* Metals 135-136 (2003) 39-40. Polypyrrole can also be deposited on gold. In some embodiments, adhesion of the electrodeposited polypyrrole layer is enhanced by covering a metal such as gold with a chemisorbed layer of molecules that can be copolymerized into the polymer layer with chemical bonding. Thiol is one example of a head group for strong chemisorbtion to metal. The tail group may be chemically similar to structured groups formed in the specific EAP employed. The use of a pyrrole ring attached to a thiol group (e.g., via a short alkyl chain) is an example for a polypyrrole EAP. Specific examples of such molecules are 1-(2-thioethyl)-pyrrole and 3-(2-thioethyl)-pyrrole. See, e.g., E. Smela et al., "Thiol Modified Pyrrole Monomers: 1. Synthesis, Characterization, and Polymerization of 1-(2-Thioethyl)-Pyrrole and 3-(2-Thioethyl)-Pyrrole," *Langmuir,* 14 (11), 2970-2975, 1998.

Various dopants can be used in the polypyrrole-containing active regions, including large immobile anions and large immobile cations. According to one specific embodiment, the active region comprises polypyrrole (PPy) doped with dodecylbenzene sulfonate (DBS) anions. When placed in contact with an electrolyte containing small mobile cations, for example, $Na^+$ cations, and when a current is passed between the polypyrrole-containing active region and a counter electrode, the cations are inserted/removed upon reduction/oxidation of the polymer, leading to expansion/contraction of the same. This process can be represented by the following equation:

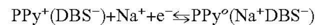

$$PPy^+(DBS^-)+Na^++e^- \leftrightarrows PPy^o(Na^+DBS^-)$$

where $Na^+$ represents a sodium ion, $e^-$ represents an electron, $PPy^+$ represents the oxidized state of the polypyrrole, $PPy^o$ represents the reduced state of the polymer, and species are enclosed in parentheses to indicate that they are incorporated into the polymer. In this case the sodium ions are supplied by the electrolyte that is in contact with the EAP member. Specifically, when the EAP is oxidized, the positive charges on the backbone are at least partially compensated by the $DBS^-$ anions present within the polymer. Upon reduction of the polymer, however, the immobile $DBS^-$ ions cannot exit the polymer to maintain charge neutrality, so the smaller, more mobile, $Na^+$ ions enter the polymer, expanding the volume of the same. Upon re-oxidation, the $Na^+$ ions again exit the polymer into the electrolyte, reducing the volume of the polymer.

EAP-containing active regions can be provided that either expand or contract when an applied voltage of appropriate value is interrupted depending, for example, upon the selection of the EAP, dopant, and electrolyte.

Additional information regarding EAP actuators, their design considerations, and the materials and components that may be employed therein, can be found, for example, in E. W. H. Jager, E. Smela, O. Inganas, "Microfabricating Conjugated Polymer Actuators," *Science,* 290, 1540-1545, 2000; E. Smela, M. Kallenbach, and J. Holdenried, "Electrochemically Driven Polypyrrole Bilayers for Moving and Positioning Bulk Micromachined Silicon Plates," *J. Microelectromechanical Systems,* 8(4), 373-383, 1999; U.S. Pat. No. 6,249,076, assigned to Massachusetts Institute of Technology, and *Proceedings of the SPIE*, Vol. 4329 (2001) entitled "Smart Structures and Materials 2001: Electroactive Polymer and Actuator Devices (see, e.g., Madden et al, "Polypyrrole actuators: modeling and performance," at pp. 72-83), each of which is hereby incorporated by reference in its entirety.

Furthermore, networks of conductive polymers may also be employed. For example, it has been known to polymerize pyrrole in electroactive polymer networks such as poly(vinylchloride), poly(vinyl alcohol), NAFION®, a perfluorinated polymer that contains small proportions of sulfonic or carboxylic ionic functional groups, available from E.I. DuPont Co., Inc. of Wilmington, Del.

EAPs are also discussed in detail in U.S. Patent Application Publications 2004/0143160 and 2004/0068161 and commonly assigned copending U.S. patent application Ser. No. 10/763,825, the entire content of which is incorporated by reference herein.

In some embodiments the stent, the delivery system or other portion of the assembly may include one or more areas, bands, coatings, members, etc. that is (are) detectable by imaging modalities such as X-Ray, MRI, ultrasound, etc. In some embodiments at least a portion of the stent and/or adjacent assembly is at least partially radiopaque.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the invention. Those skilled in the art may recognize other equivalents to the specific embodiment described herein which equivalents are intended to be encompassed by the claims attached hereto.

The invention claimed is:

1. A catheter tip comprising at least one section of electroactive polymer, the at least one section of electroactive polymer having a non-actuated state and an actuated state, the catheter tip defining a guide wire lumen, the guide wire lumen having a first diameter and a second diameter, the guide wire lumen having the first diameter when the at least one section of electroactive polymer is in the non-actuated state and the guide wire lumen having the second diameter when the at least one section of electroactive polymer is in the actuated state, the first diameter being greater than the second diameter, the at least one section of electroactive polymer comprising a first section and a second section, the first section expanding into the guide wire lumen a first distance when the first section is in the actuated state, the second section expanding into the guide wire lumen a second distance when the second section is in the actuated state, the first distance being greater than the second distance, wherein the first diameter of the guide wire lumen is the same for the first and second sections of electroactive polymer and the second diameter of the guide wire lumen when the first section of electroactive polymer is in the actuated state is less than the second diameter of the guide wire lumen when the second section of electroactive polymer is in the actuated state.

2. The catheter tip of claim 1 wherein the electroactive polymer is an electric electroactive polymer or an ionic electroactive polymer.

3. The catheter tip of claim 2 wherein the electroactive polymer is an ionic electroactive polymer selected from the group consisting of conductive polymers, ionic polymer gels, ionomeric polymer-metal composites, carbon nanotubes and mixtures thereof.

4. The catheter tip of claim 3 wherein the ionic electroactive polymer is a conductive polymer selected from the group consisting of polypyrroles, polyanilenes, polythiofenes, polyethylenedioxythiophenes, poly(p-phenylene vinylene)s, polysulfones, polyacetylenes and mixtures thereof.

5. The catheter tip of claim 1, the first and second sections of electroactive polymer each extending about an entire circumference of the catheter tip and each having a different longitudinal position along a length of the catheter tip.

6. The catheter tip of claim 1, the catheter tip comprising an inner surface section and an outer surface section, the inner surface section defining the guide wire lumen, the outer surface section being coextensive with and disposed about the inner surface section, the at least one section of electroactive polymer forming the inner surface section.

7. The catheter tip of claim 1 comprising an inner surface section, the inner surface section defining the guide wire lumen, the inner surface section comprising the at least one section of electroactive polymer, each section of the at least one section of electroactive polymer forming a band extending about the entire circumference of the guide wire lumen.

8. The catheter tip of claim 7 comprising an outer surface section, the inner surface section constructed from a different material than the outer surface section.

9. The catheter tip of claim 1, comprising an inner surface section, the inner surface section defining the guide wire lumen, the inner surface section comprising the at least one section of electroactive polymer, wherein the at least one section of electroactive polymer forms at least one circumferential coil.

10. A catheter tip comprising at least one section of electroactive polymer, the at least one section of electroactive polymer having a non-actuated state and an actuated state, the catheter tip defining a guide wire lumen, the guide wire lumen having a first diameter and a second diameter, the guide wire lumen having the first diameter when the at least one section of electroactive polymer is in the non-actuated state and the guide wire lumen having the second diameter when the at least one section of electroactive polymer is in the actuated state, the first diameter being greater than the second diameter, the at least one section of electroactive polymer comprising a first layer of electroactive polymer and a second layer of electroactive polymer, each layer of electroactive polymer extending about an entire circumference of the catheter tip, each layer of electroactive polymer being separately actuatable, the first layer of electroactive polymer being coextensive with and radially adjacent to the second layer of electroactive polymer, the guide wire lumen having the second diameter when the first layer of electroactive polymer is in the actuated state, the guide wire lumen further having a third diameter when the second layer of electroactive polymer is in the actuated state, the second diameter being greater than the third diameter.

11. A catheter tip comprising at least one section of electroactive polymer, the at least one section of electroactive polymer having a non-actuated state and an actuated state, the catheter tip defining a guide wire lumen, the guide wire lumen having a first diameter and a second diameter, the guide wire lumen having the first diameter when the at least one section of electroactive polymer is in the non-actuated state and the guide wire lumen having the second diameter when the at least one section of electroactive polymer is in the actuated state, the first diameter being greater than the second diameter, the at least one section of electroactive polymer comprising a first section and a second section, the first section constructed and arranged to engage a guide wire having a first diameter when the first section is in the actuated state, the second section constructed and arranged to engage a guide wire having a second diameter when the second section is in the actuated state, the first guide wire diameter being greater than the second guide wire diameter.

12. A method of using a catheter with an electroactive catheter tip comprising the steps of:

providing a catheter, the catheter comprising a catheter tip and an interior surface, the catheter tip comprising at least one section of electroactive polymer, the at least one section of electroactive polymer having a non-actuated state and an actuated state, the interior surface defining a guide wire lumen;

providing a guide wire, the guide wire having a diameter, positioning the guide wire within the guide wire lumen;

inserting the catheter into a bodily vessel;

advancing the catheter within the bodily vessel; and causing the at least one section of electroactive polymer to change from the non-actuated state to the actuated state, the at least one section of electroactive polymer engaging the guide wire in the actuated state, the at least one section of electroactive polymer comprising a first section and a second section, the first section of electroactive polymer constructed and arranged to engage the guide wire when the diameter of the guide wire is a first diameter, the second electroactive polymer constructed and arranged to engage the guide wire when the diameter of the guide wire is a second diameter, the second diameter being greater than the first diameter;

wherein only one of the first and second sections of electroactive polymer is caused to change from the non-actuated state to the actuated state depending on the diameter of the guide wire provided.

13. The method of claim 12 wherein the electroactive polymer is an electric electroactive polymer or an ionic electroactive polymer.

14. The method of claim 13 wherein the electroactive polymer is an ionic electroactive polymer selected from the group consisting of conductive polymers, ionic polymer gels, ionomeric polymer-metal composites, carbon nanotubes and mixtures thereof.

15. The method of claim 14 wherein the ionic electroactive polymer is a conductive polymer selected from the group consisting of polypyrroles, polyanilenes, polythiofenes, polyethylenedioxythiophenes, poly(p-phenylene vinylene)s, polysulfones, polyacetylenes and mixtures thereof.

* * * * *